United States Patent [19]

Zemanian et al.

[11] Patent Number: 5,073,666
[45] Date of Patent: Dec. 17, 1991

[54] HYDROCARBON SYNTHESIS FROM LOWER ALKANES AT ADVANCED TEMPERATURES AND HIGH PRESSURES

[75] Inventors: Thomas S. Zemanian, Port Jefferson, N.Y.; Thomas Gold, Ithaca; William B. Streett, Ithaca; John A. Zollweg, Ithaca, N.Y.

[73] Assignee: Cornell Research Foundation, Inc., Ithaca, N.Y.

[21] Appl. No.: 697,737

[22] Filed: May 3, 1991

Related U.S. Application Data

[63] Continuation of Ser. No. 380,190, Jul. 14, 1989, abandoned.

[51] Int. Cl.$^5$ .......................... C07C 2/00; C07C 2/02; C07C 2/54
[52] U.S. Cl. .................... 585/734; 585/400; 585/500; 585/700; 585/743; 585/671; 585/943
[58] Field of Search ............. 585/943, 743, 700, 500, 585/502, 400, 671, 734, 735

[56] References Cited

U.S. PATENT DOCUMENTS

| 2,373,303 | 4/1945 | Frey et al. ........................ 260/671 |
| 3,209,046 | 9/1965 | Bryson et al. ...................... 260/671 |
| 3,251,897 | 5/1966 | Wise ................................ 260/671 |
| 3,396,206 | 8/1968 | Scott ................................ 260/669 |
| 4,524,230 | 6/1985 | Haensel ............................ 585/467 |
| 4,769,507 | 9/1988 | Murib et al. ....................... 585/500 |
| 4,780,449 | 10/1988 | Hicks .............................. 502/303 |
| 4,822,938 | 4/1989 | Audeh et al. ...................... 585/324 |
| 4,822,941 | 4/1989 | Baillargeon et al. ............... 585/417 |

OTHER PUBLICATIONS

Journal of Catalysis, vol. 73, "Synthesis of Ethylen via Oxidative Coupling of Methane," Keller and Bhasin, pp. 9–19 (1982).
NTIS Report No. SAND-88-7092C by David Gray et al., May 20, 1988.
Gold, Thomas et al., Geochimiia et Cosmechimica Acta vol. 50, pp. 2411–2418 (1986).

Primary Examiner—Asok Pal
Attorney, Agent, or Firm—Jones, Tullar & Cooper

[57] ABSTRACT

Upon a pressure vessel reactor, lower alkanes such as methane and propane subjected to temperatures of up to 800 K and pressures up to 70,000 psi (467 MPa), isomerize even in the absence of catalyst to produce a variety of alkanes, alkenes, cycloalkanes and aromatic hydrocarbons containing up to twelve carbon atoms.

15 Claims, 10 Drawing Sheets

HYDROCARBON SYNTHESIS FROM LOWER ALKANES AT ADVANCED TEMPERATURES AND HIGH PRESSURES

This application is a continuation of application Ser. No. 07/380,190, filed July 14, 1989, now abandoned.

This invention relates to the isomerization of lower alkanes even in the absence of catalyst to give a variety of hydrocarbons containing up to twelve carbon atoms.

BACKGROUND OF THE INVENTION

Methane is a very stable molecule with a C—H bond energy of 105 kcal/mole relatively inert to chemical reaction at temperatures where thermal dissociation is negligible. In the absence of a catalyst measurable dissociation of methane does not occur below 525° C. (Egloff, Reactions of Pure Hydrocarbons, pp 38-39, 1937). Methane reaction with saturated hydrocarbons such as alkanes and cycloalkanes has not been detected. Unsaturates like acetylenes and lower olefins, however, react with methane at ambient temperatures, but under exceptional catalytic conditions —a Ziegler-Natta system for acetylene insertion into methane (Grigoryan et al, 1981) or a strong acid system, $TaF_5$—HF for alkylation by olefins (Siskin and Mayer, 1978). Aromatics, the major unsaturated hydrocarbon constituents of petroleum, do not react with methane at ordinary temperatures and pressures. The alkylation of benzene with methane, however, could occur either under conditions such as high-frequency electrodeless gaseous discharge (Prilezhaeva and Noether, 1937) or in the presence of catalysts, such as $NiO$—$Al_2O_3$ (Rieche and Seeboth, 1963), or $Ni$-$Al_2O_3$ (Rieche et al., 1964) or a strong acid system, for example, anhydrous fluoroantimonic acid (Olah et al., 1975). The addition of methane to benzene under non-pyrolytic as well as pyrolytic conditions (MacKenzie and Growcock, 1977) has resulted in the formation of toluene in varying yields. Alkylation of phenol with methane over solid acids and bases such as $SiO_2$—$Al_2O_3$, $MgO$—$Al_2O_3$, $SiO_2$—$Al_2O_3$ and MgO at temperatures where significant methane pyrolysis occurs (above 650° C.) produced mixtures of cresols and xylenols in varying yields (Nishizaki and Tanabe, 1973). Recently Dabrowski (1980) has reported selective orthoalkylation of phenols by methane catalyzed by NiO supported on MgO, to 2,6-xylenol. In all these cases the addition of methane onto the aromatic ring resulted in the incorporation of "one carbon unit", or methylation of the ring.

In order to assess the possible role of methane in petroleum formation, Gold et al (Geochimica et Cosmochimica Acta Vol. 50, 2411-2418 (1986)) studied the reaction of methane with liquid aromatic hydrocarbons at 15,000 psi (100 MPa) and 150-250° C. in the presence of montmorillonite clay catalyst using $^{14}C$ labeled methane to trace reaction products. Reaction of methane with benzene gave predominantly $C_2$ addition while only very small amounts of $C_1$ addition were detected.

Because of the availability of lower alkanes, there is a need to synthesize higher hydrocarbon from these resources. Prior art references have suggested that hydrocarbons subjected to high pressures and temperatures greater than 300° C. (573 K) would equilibrate to mixtures of methane and carbon (soot) The present invention relates to the conversion of $C_1$-$C_3$ hydrocarbons or mixtures thereof in the absence of catalyst to give higher hydrocarbons.

BRIEF DESCRIPTION OF THE INVENTION

One object of the present invention relates to a process for converting a feedstock comprising one or more $C_1$-$C_3$ hydrocarbons to a product hydrocarbons having up to 12 carbon atoms which comprises heating even in the absence of catalyst one or more $C_1$-$C_3$ alkane hydrocarbons at a temperature from about 673 K to about 723 K, preferably about 673 K at a pressure from about 40,000 psi (267 MPa) to about 70,000 psi (467 MPa), preferably about 60,000 psi (400 MPa); wherein said product comprises at least one of the following: branched or straight chain alkane hydrocarbons; branched or straight chain unsaturated aliphatic hydrocarbons; cycloalkanes and aromatic hydrocarbons.

Another object relates to the conversion of propane or methane to higher hydrocarbons.

A yet further object relates to the conversion of mixtures of methane and propane to higher hydrocarbons.

DETAILED DESCRIPTION OF THE INVENTION

The invention relates to the conversion of lower alkane hydrocarbons to higher product hydrocarbons by reacting one or more $C_1$-$C_3$ hydrocarbons in the absence of catalyst at temperature of from about 673 K to about 873 K, preferably about 673 K and pressures of from about 40,000 psi (267 MPa) to about 70,000 psi (467 MPa), preferably about 60,000 psi (400 MPa) for a time sufficient to produce the desired hydrocarbon product or mixtures thereof including those products shown in the best mode examples.

By hydrocarbon products or product hydrocarbons is meant one or more hydrocarbons containing up to about 12 carbon atoms or their unsaturated counterparts obtained by reacting $C_1$-$C_3$ hydrocarbons or mixtures thereof under the temperature and pressure conditions set forth herein. While it is not certain how the variety of products are formed, it is believed that the higher hydrocarbons result by addition of $C_1$ and $C_2$ fragments generated during the course of the reaction.

A second aspect of the invention relates to the non-catalyzed addition of methane to paraffin hydrocarbons to yield hydrocarbon products resulting from both $C_1$ and $C_2$ carbon additions.

As shown in the best mode examples, mixtures of methane and propane react at pressure and temperatures up to about 773 K primarily by alkylation of the propane at the secondary carbon.

As shown in Table 1, 80%/20% methane/propane mixtures at 700 K, 400 MPa and 95 minute reaction time show a decrease in methane content, increase in propane content and the production of isopentane, butane, isobutane and pentane. As shown in Table 2 of Example 2, a 50%/50% methane/propane mixture at 723 K and (400 MPa) pressure appears to produce small quantities of benzene and hexane at 132 hours and 183 hours reaction time.

By heating methane alone for two weeks at a temperature of 673 K and 32000 psi (213 MPa), no rearrangement products were detected. It would appear that methane is favored under these conditions.

By controlling the temperature and pressure and without the addition of catalyst, it is possible to convert one or more lower alkanes ($C_1$–$C_3$) to a variety of hydrocarbons including alkanes, alkenes, cycloalkanes, cycloalkenes and aromatic hydrocarbons. Examples of alkanes which can be produced include, methane, ethane, propane, butane, isobutane (secondary butane), pentane, isopentane, neopentane, hexane, isohexane, and the like.

Figure 4:
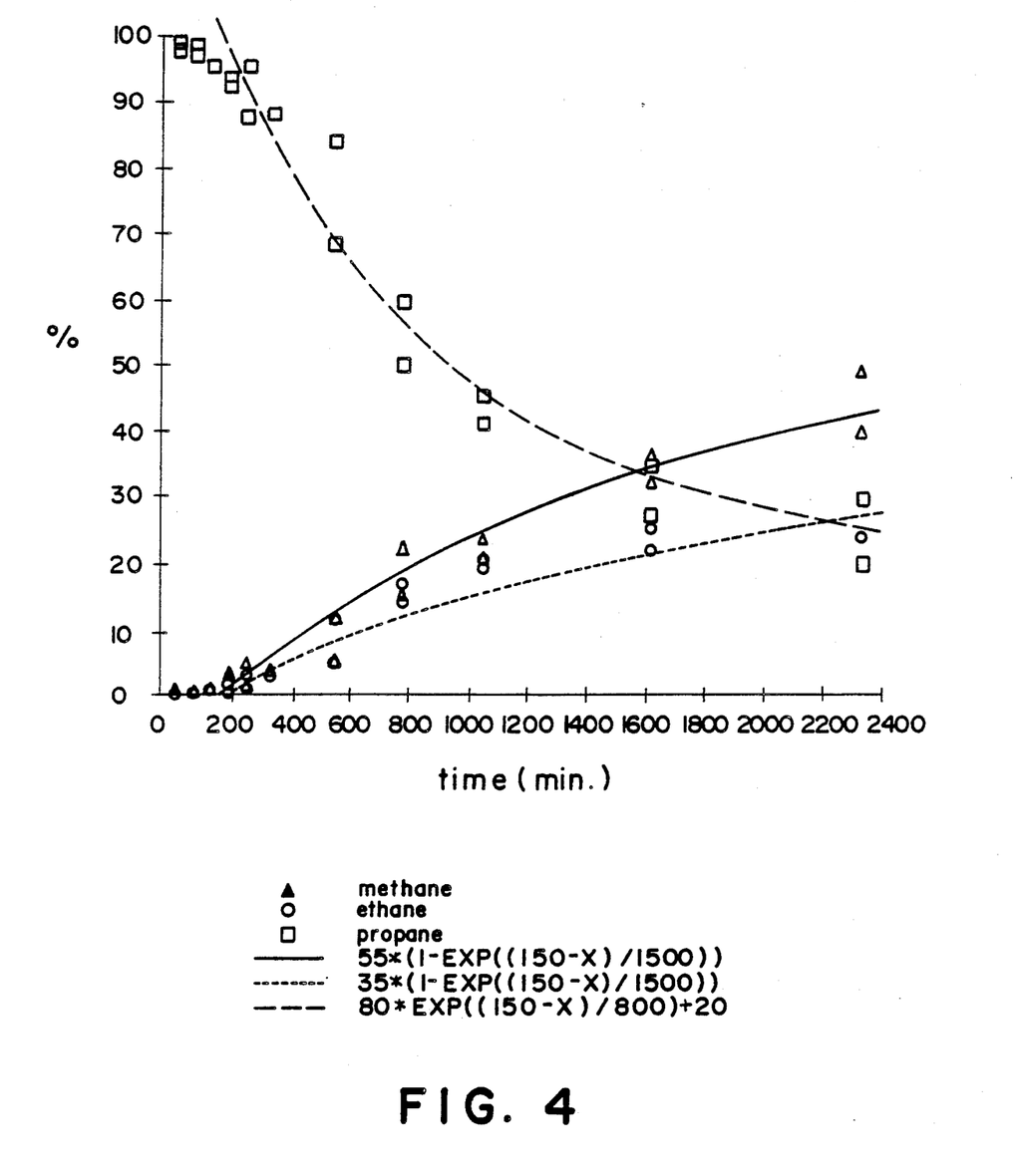
FIGS. 4 thru 11 show distribution of synthesized higher hydrocarbons versus time by reacting propane at 723 K and 60,000 psi (400 MPa).
Figure 5:
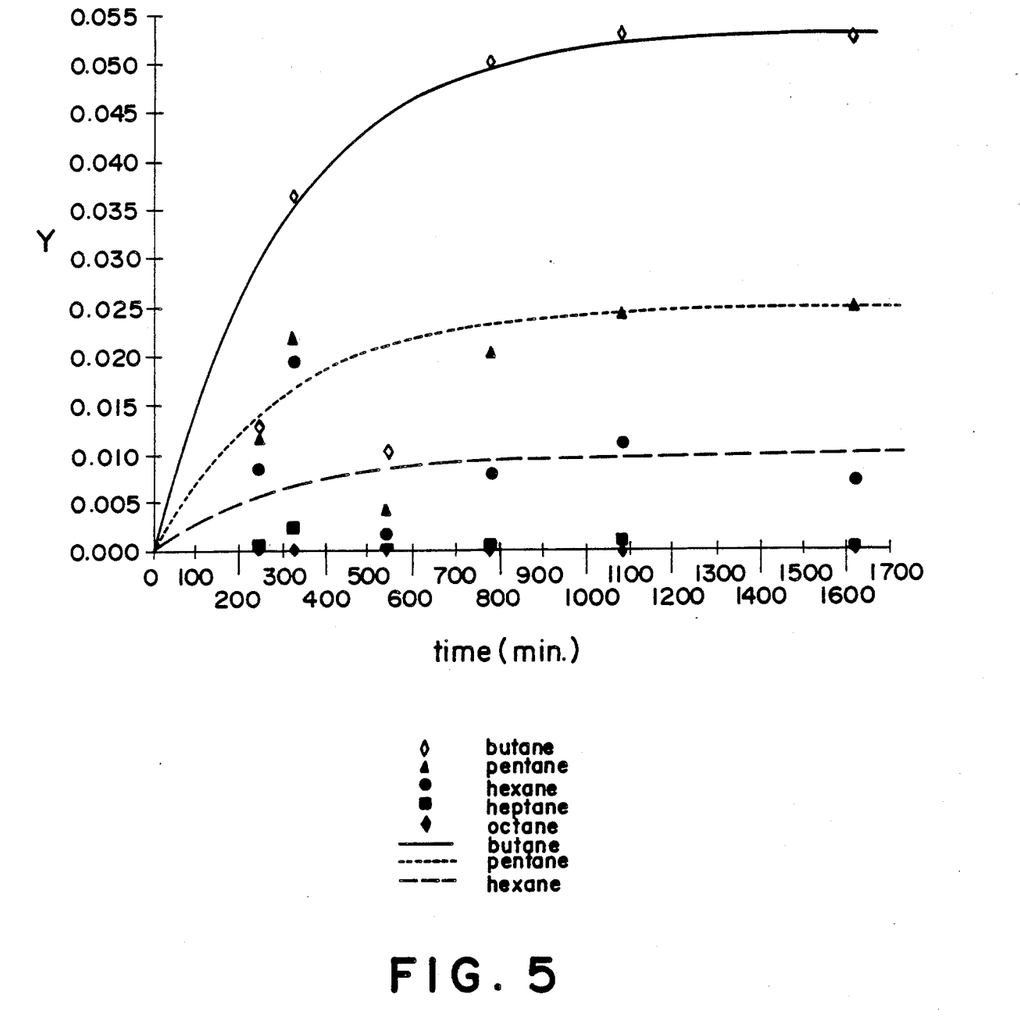
Figure 6:
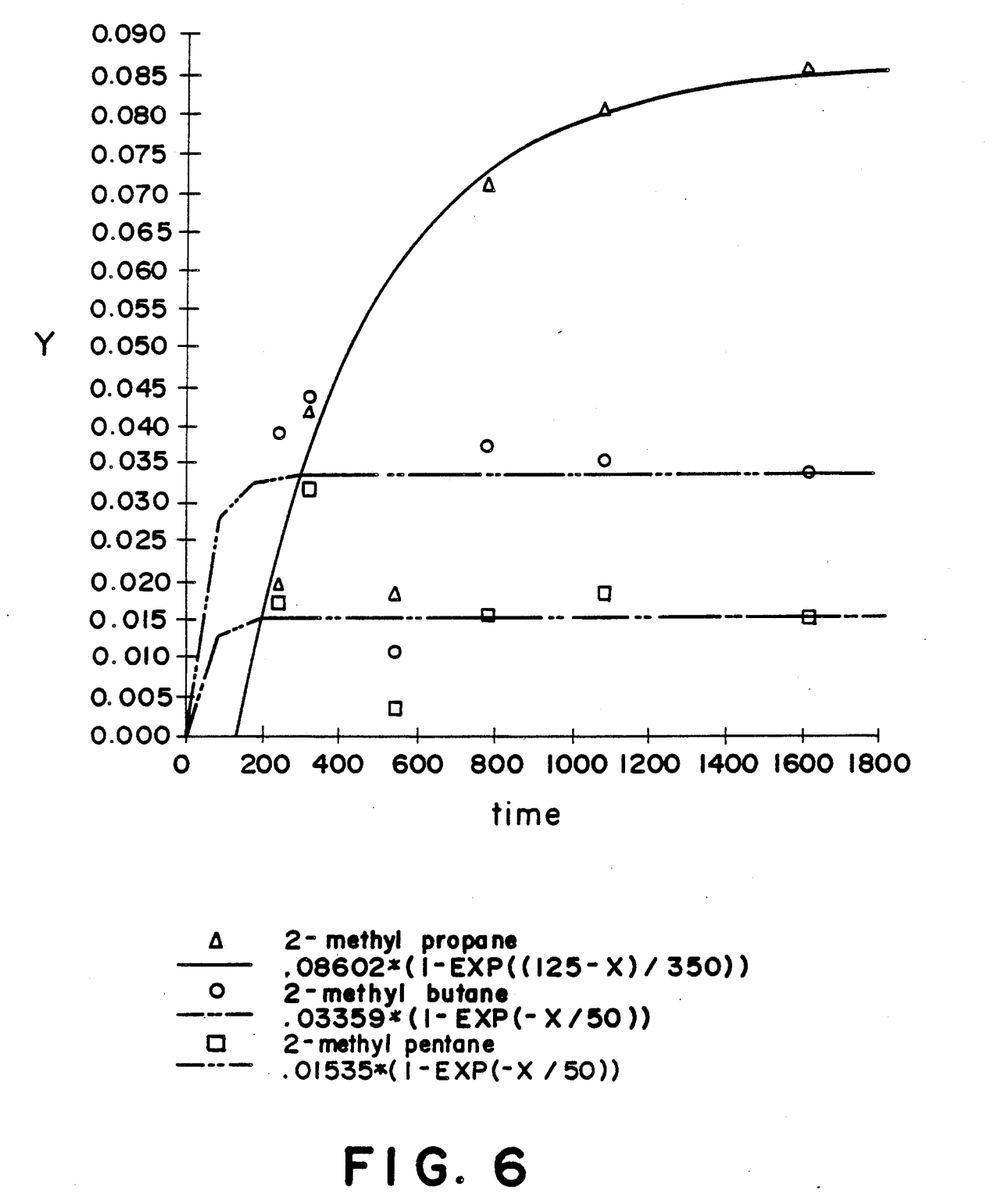
Figure 7:
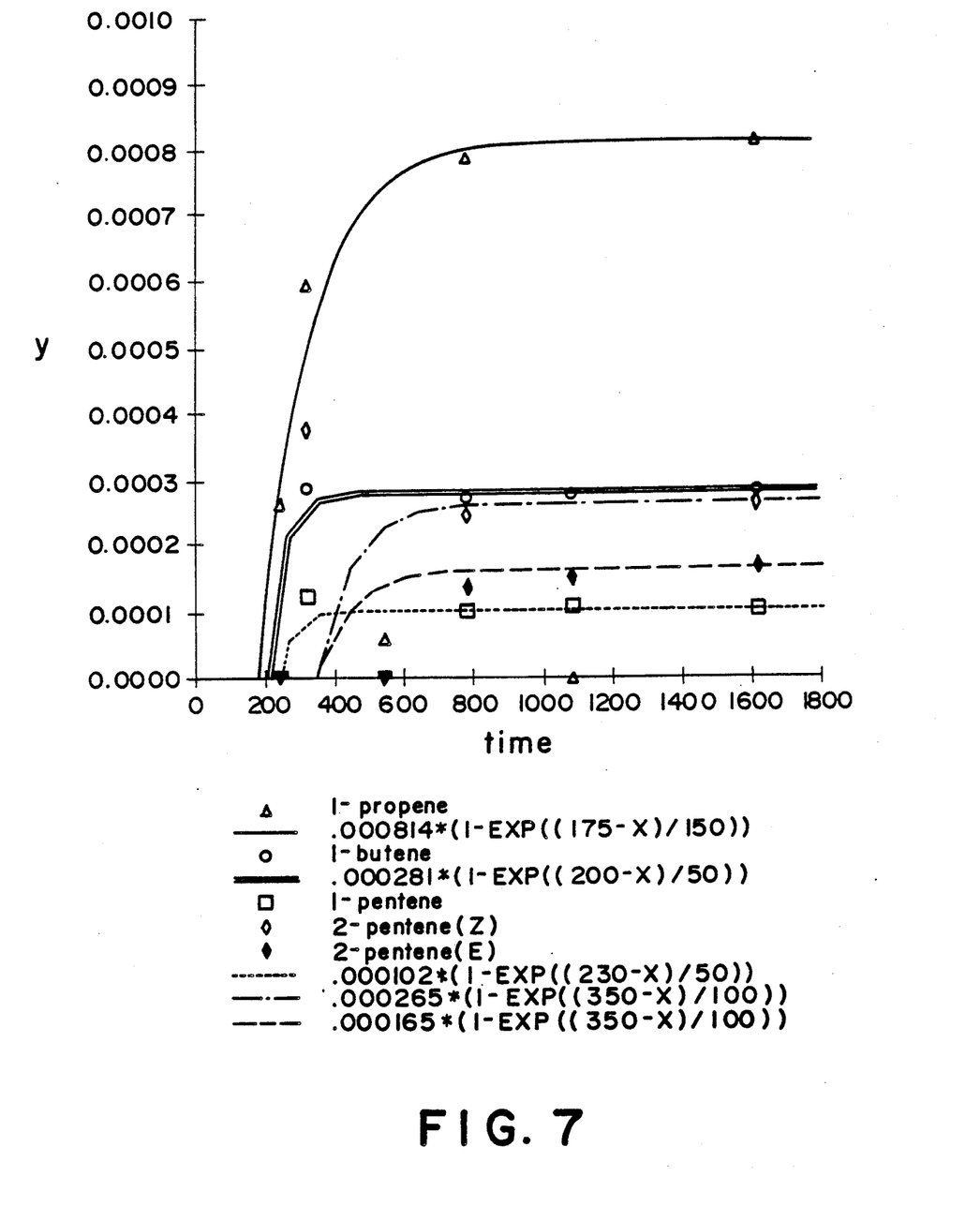
Figure 8:
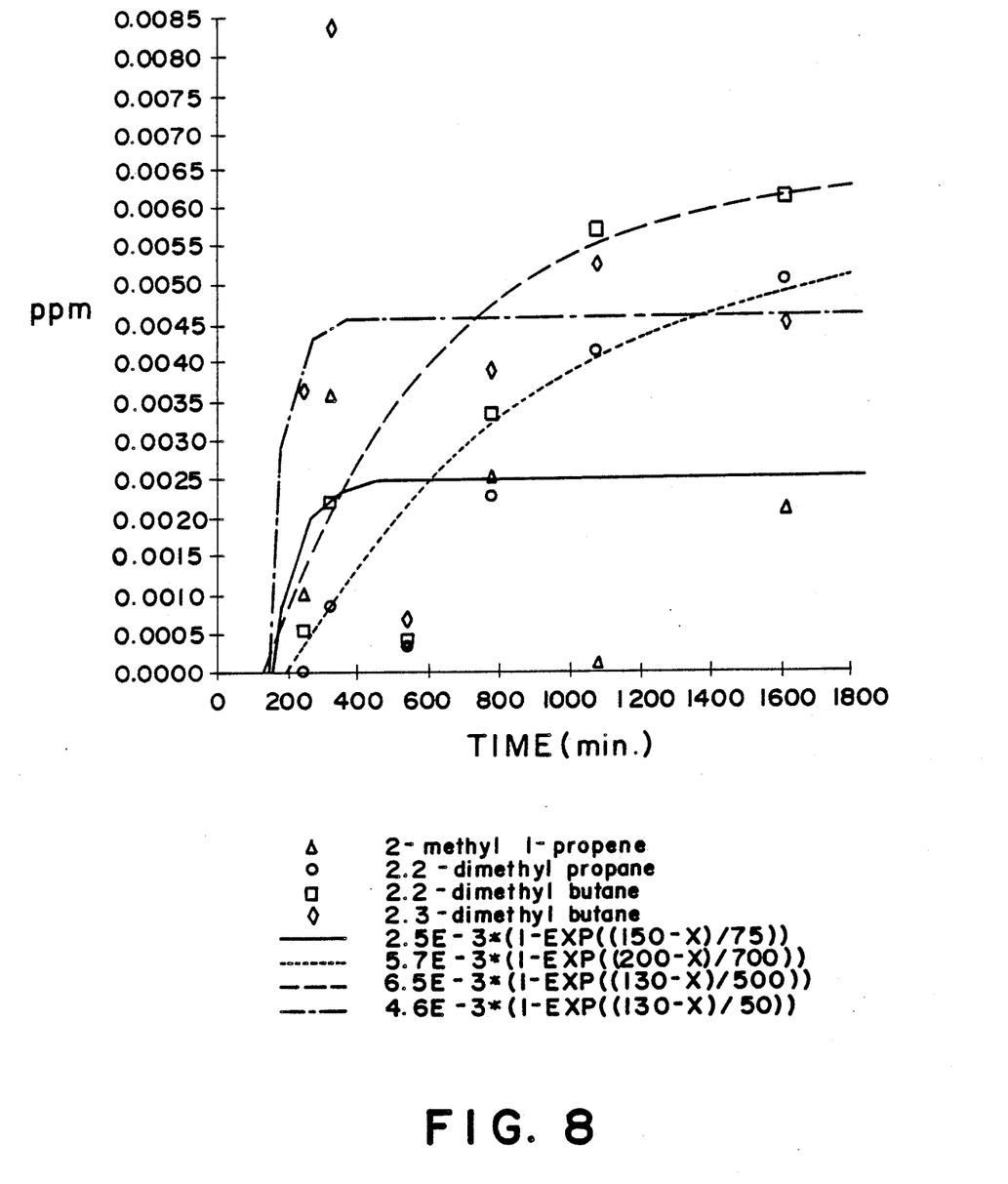
Figure 9:
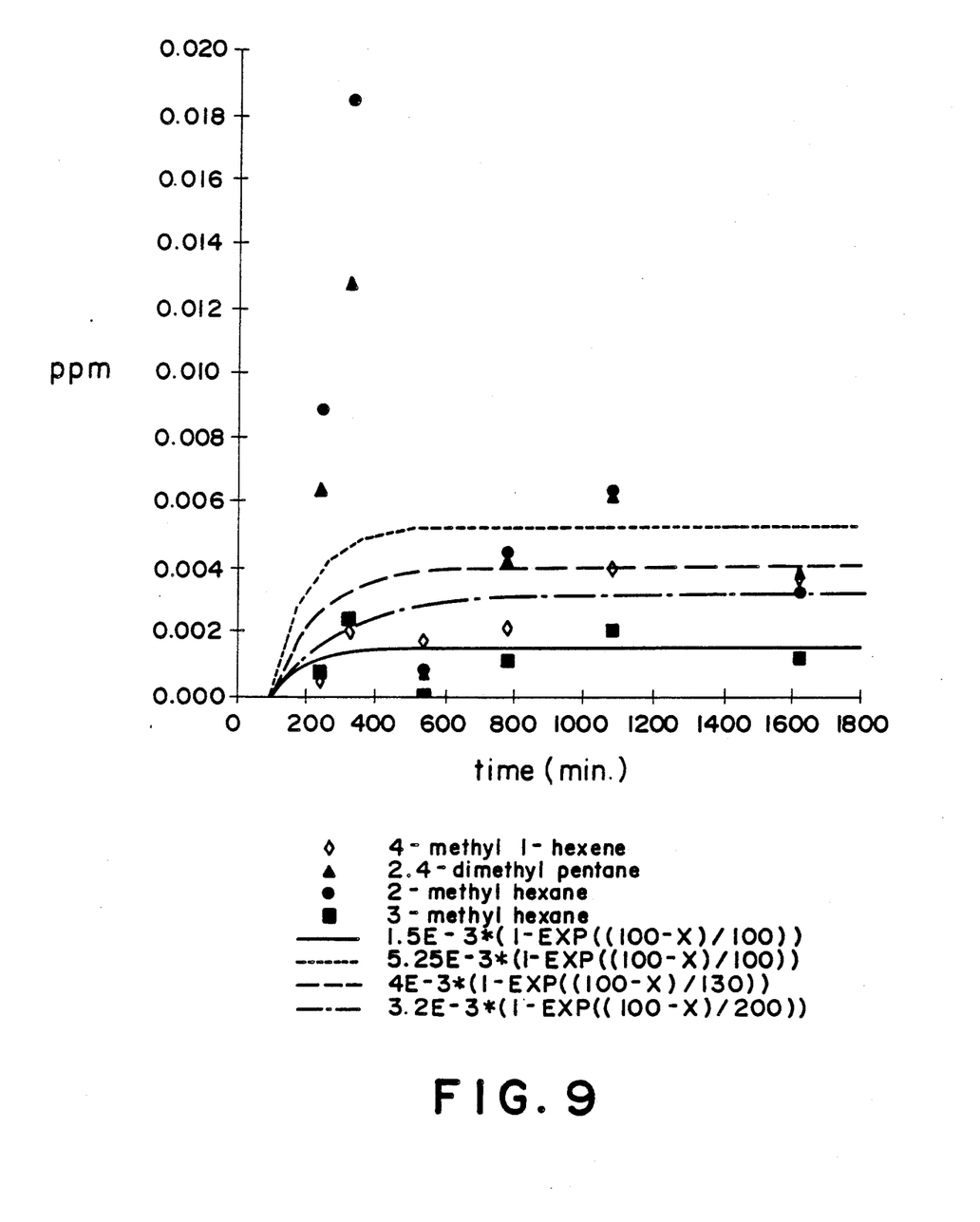

As shown in Example 5, the reaction of pure propane in the gold lined reactor at 723 K and 60000 psi (400 MPa) produce an entire sequence of products ranging from propane to cyclopentane and cyclohexane, and aromatics such as benzene and methylbenzene (see Table 4). The various products and their appearance and disappearance as the reaction proceeds over a thirty hour period are shown in a series of product plots versus time, FIGS. 4 through 11. FIG. 4 shows the time relationship of methane, ethane and propane. FIG. 5 shows the time plots for butane, pentane, hexane, heptane and octane. FIG. 6 shows that 2-methyl propane increases in amounts greater than 2-methyl butane and 2-methyl pentane. FIG. 7 shows the production of unsaturated products containing up to 5 carbon atoms, namely 1-propene; 1-butene; 2-pentene; and 1-pentene in that order. FIG. 8 shows the production of branched species, namely 2,2-dimethyl butane, 2,3-dimethyl butane, 2,2-dimethyl propane, and 2-methyl 1-propene. FIG. 9 shows the production of higher branched species, namely 4-methyl 1-hexane, 2,4- dimethyl pentane, 2-methyl hexane, and 3-methyl hexane.

Figure 10:
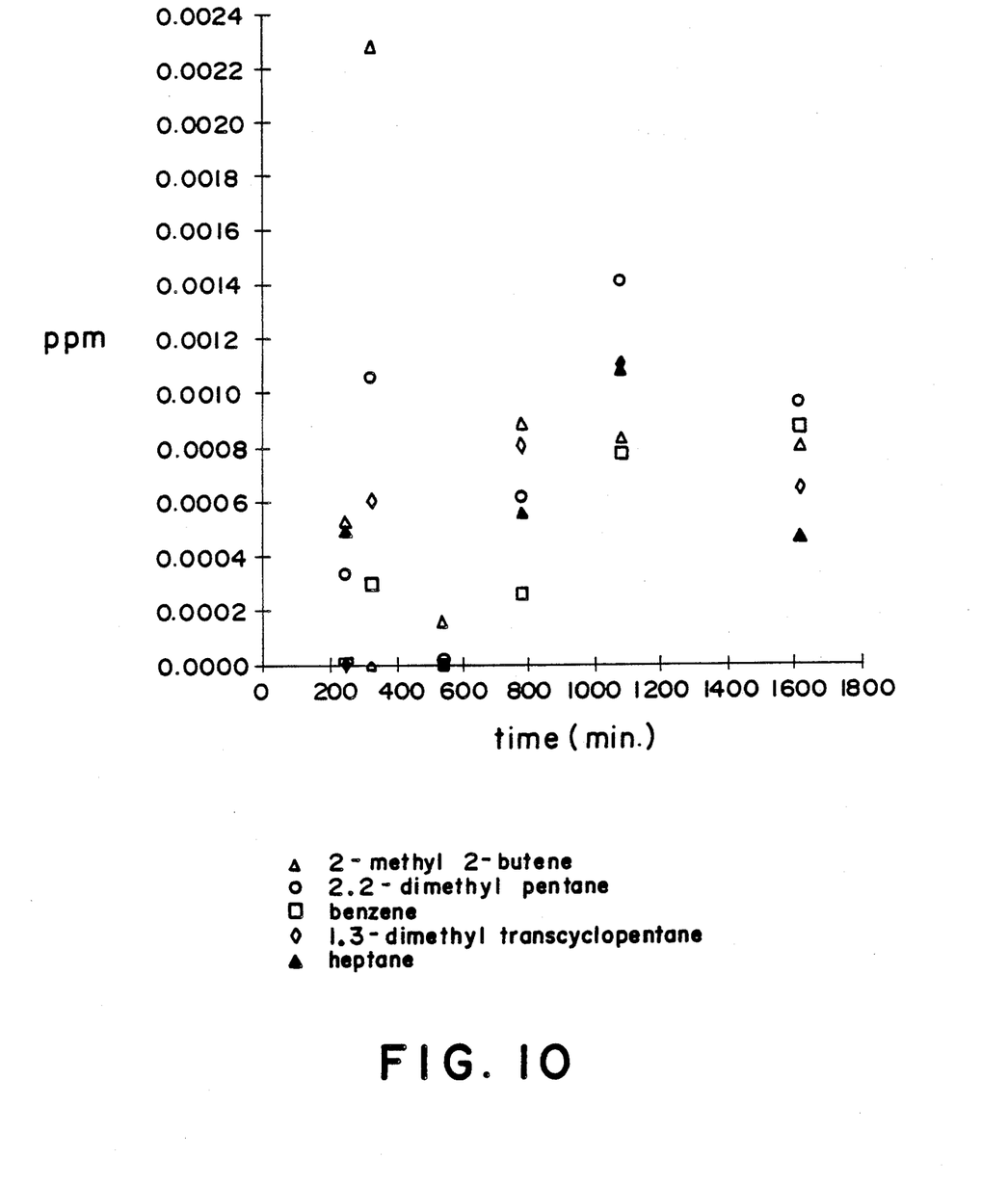

FIG. 10 shows trace species of cycloalkanes, $C_7$ alkanes and aromatics, namely heptane, 2-methyl 2-butane, 2,2-dimethyl pentane, benzene, and 1,3-dimethyl transcyclopentane.

Figure 11:
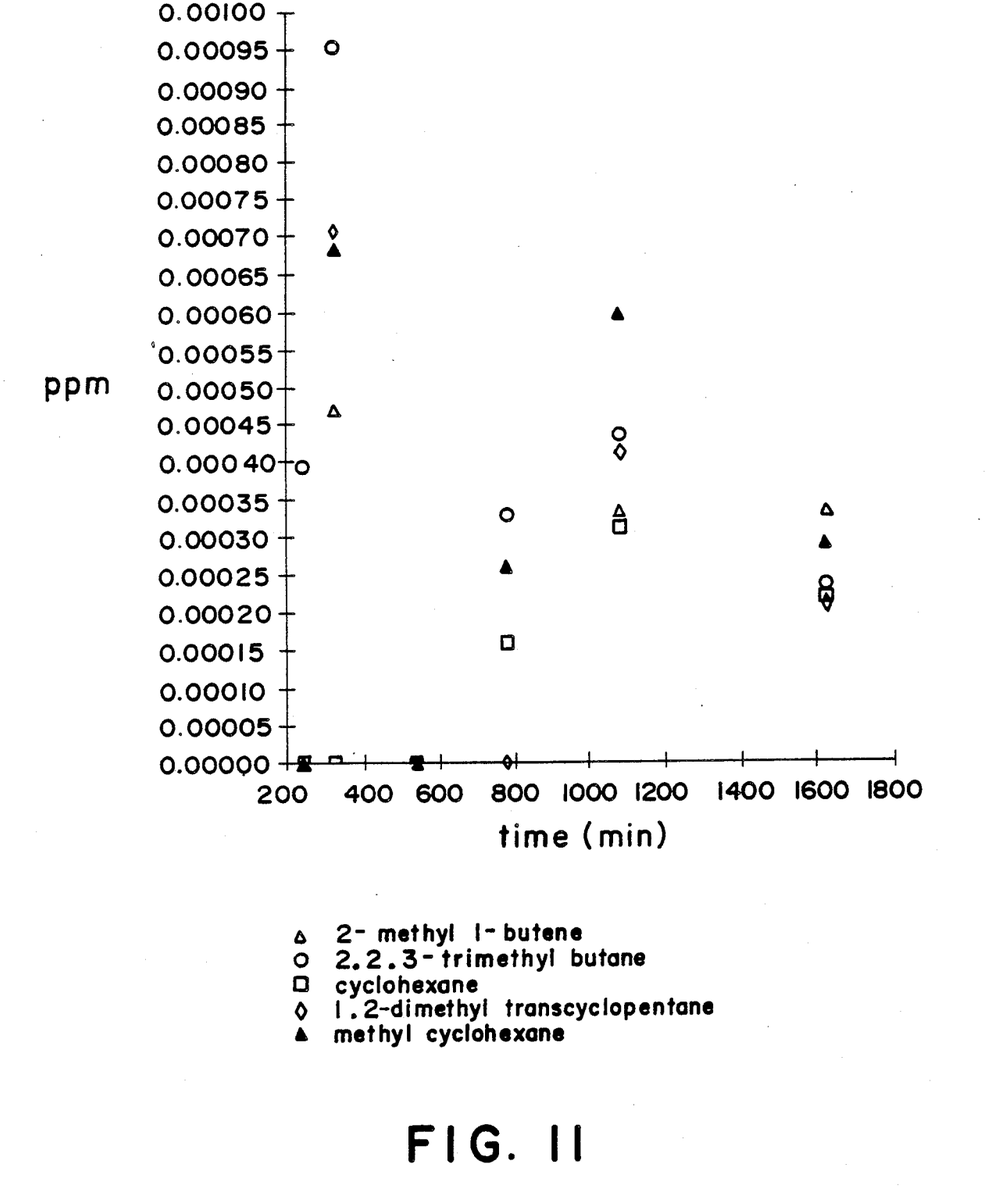

FIG. 11 shows production of other trace species, namely, 2,2,3-trimethyl butane, methyl cyclohexane, 1,2-dimethyl transcyclopentane, 2-methyl-l-butane, and cyclohexane.

The alkylation apparatus comprises a vessel of Inconel 718, preferably internally coated with a layer of metal such as gold to prevent hydrogen permeation. The apparatus is equipped with ancillary pressure generation equipment capable of the full range of pressures of interest, namely pressures up to 150,000 psi (1.0 GPa) and preferably in the range of from about 15,000 (100 MPa) to about 100,000 psi (667 MPa). The apparatus is shown in FIGS. 1 and 2.

Figure 1:
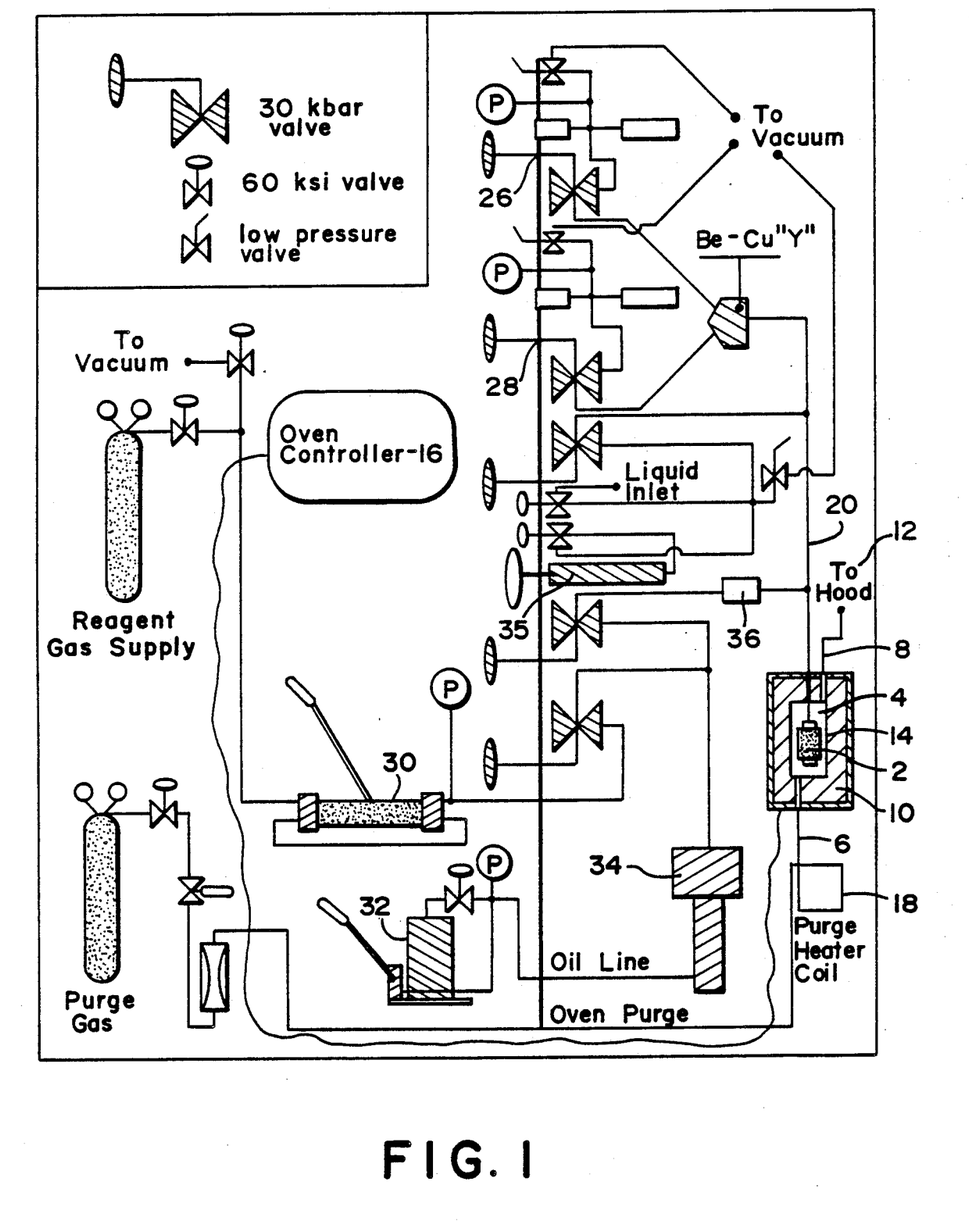
FIG. 1 represents a schematic diagram of the system used for hydrocarbon synthesis under high pressure and temperature.

FIG. 1 represents a schematic diagram of the Inconel 718 reactor system for hydrocarbon synthesis under high pressure and temperature. The reactor vessel (2), surrounded by oven atmosphere chamber (4) having controlled atmosphere input (6) and exhaust port (8), is enclosed within oven (10) having a heater mechanism (14) controlled by oven controller (16). Controlled atmosphere ($N_2$, $CO_2$, etc.) inlet (6) is provided with a preheater (18). Chamber 4 surrounding reaction vessel (2) is ducted to exit port (8) using exhaust fan (12). Reactor inlet capillary (20), used for charging the reactor, also contains hypodermic needle sampling lines connected to sample ports (26) and (28). Reactant pressure is provided by compressor (30) or screw driven pump (35), augmented by pressure intensifier (34), through inlet tube (20) to the reactor vessel (2). Pressure is measured wing manganin pressure gauge (36).

Figure 2:
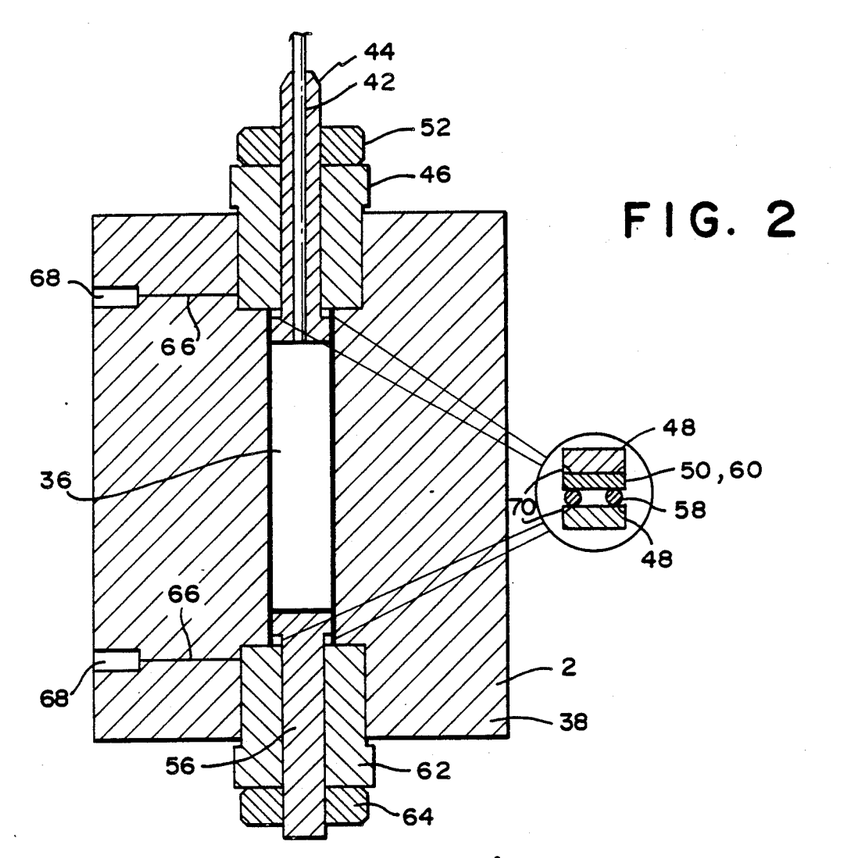
FIG. 2 represents a cross-sectional side view of the high pressure vessel with gold coated reaction chamber.

FIG. 2 represents a cross section side view of the Inconel 718 reactor system (2) comprising a 3" long cylindrical chamber (36) internally coated or plated with a metal such as silver or gold; said cylinder being the cavity derived from Inconel block (38), closed at the top by a seal consisting of hollow mushroom stem (44) with internal gold plating (42) allowing for loading methane and hydrocarbon starting materials, said stem positioned and held in place by drive nut (46) and sealed by Inconel 718 spacers (48) and surrounding metal (Ag) ring seals (50) assembly, said seal tightened initially using mild steel spacer (52). Chamber (36) is sealed at the bottom by dead end plug (56) with Au wire rings (58), silver seal (60) and brass anti-extrusion rings (70) atop Inconel 718 drive nut (62). The seal at dead end plug (56) is tightened initially by mild steel nut (64). Weep holes (66) access the regions just outside the seals and allow gas to exit through the exhaust port (68) to detect chamber integrity.

An electric oven controls the temperature of the vessel within 5 K and serves as part of the safety shielding. Samples were taken from either the top or the bottom of the vessel volume using hypodermic needle tubing which enters the vessel through the vessel fill line (20). Samples were analyzed on a gas chromatograph equipped with a mass spectrometer detector and/or by a gas chromatograph alone. Detection limits are on the order of parts per million.

The pressure reactor (2) is a thick-walled monoblock autofrettaged vessel of Inconel 718, with an internal volume of approximately 10 $em^3$, gold plated internal surfaces, a wall ratio of 8:1, and a calculated burst pressure of better than 1.5 GPa at 1000 K. The vessel resides in a steel jacketed electrical oven (10) with on/off temperature control. The temperature is stable to within 5 K under normal operation. The oven is flushed with an inert gas to minimize the possibility of combustion should a leak develop at high temperature. Although the pressure generation equipment is capable of developing pressures up to 2 GPa, operation with pressures above 1 GPa is not recommended. Hypodermic needle tubing enters the vessel through the inner bore of the connecting tubing (20) and allows for sampling of the vessel contents during operation. The samples may be drawn from either the top or the bottom of the vessel, allowing detection of phase instability. Due to the extremely small bore of the hypodermic needle tubing, the samples are easily throttled from the vessel pressure into an evacuated chamber, to attain a final pressure of 15 psig (200 kPa). These samples may then be drawn into syringes at (26) or (28) and injected into a gas chromatograph for analysis. All portions of the apparatus that are exposed to the high pressure fluid reside behind shielding of ⅛inch steel clad with ⅜inch plywood. The oven effluent (due to the inert purge) is ducted (8) to the outdoors. The apparatus is operated entirely from outside the safety shielding.

Temperature measurement is accomplished using a thermocouple in physical contact with the vessel. The pressure is measured using a manganin wire coil (36) external to the oven. The temperature may also be measured at the heated purge gas inlet (6) on the oven to prevent development of a thermal gradient within the oven. Temperature control is accomplished using a platinum resistance temperature device (RTD) as one leg of a Wheatstone bridge. The bridge output is fed to a comparator, which in turn operates a relay through which the oven heaters are powered. Thus, the control is of the simple on/off type.

SAMPLING AND PRODUCT ANALYSIS

The sampling method consists of drawing samples from within the vessel, either at the top or the bottom portions of the vessel interior, through hypodermic needle tubing. The tubing is of 304 stainless steel, 0.009 inches in O.D. with a 0.004 inch thick wall, is gold plated on the outer diameter, and accesses the vessel through the interior of the ⅛inch capillary tubing that connects the vessel to the pressure generation and measurement equipment. After leaving the vessel, the two lines pass through the ⅛inch cross fitting and diverge at the beryllium-copper Y fitting. Each then proceeds to its associated high pressure sampling valve.

Figure 3:
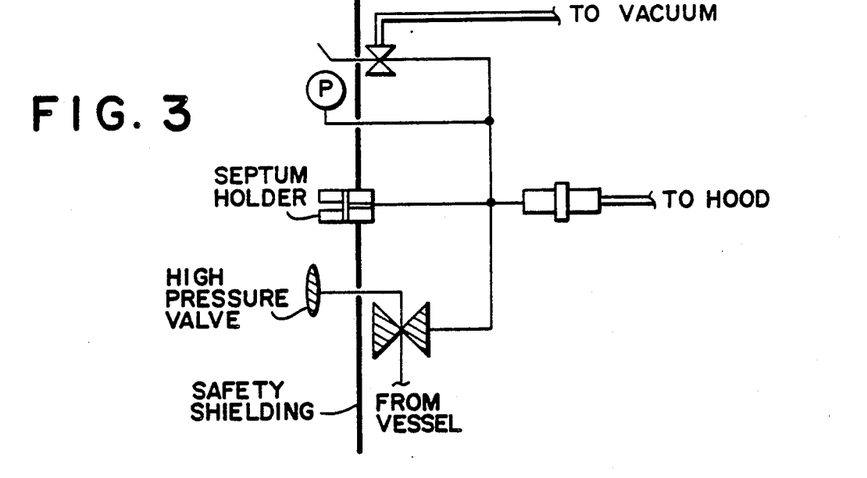
FIG. 3 represents a schematic diagram of the sampling system used.

The sampling procedure is as follows: a syringe, fitted at the needle with a gas tight valve, is connected to the system through one of the septa and the needle, syringe (with the plunger fully depressed and the valve open), sampling chamber, volume behind the septum and the associated relief valve, tubing, and sampling valve interior are evacuated (see FIG. 3). The vacuum system is then isolated and the sampling valve is cracked open until the pressure in the sampling system (as measured by the bourdon tube gauge) reaches ≈15 psig. and the relief valve cracks open. The high pressure valve is then shut, and the plunger of the syringe is withdrawn to the desired volume. The gas tight valve on the syringe is closed, the syringe is withdrawn from the septum, and the remaining sample is dumped to the vacuum system. The syringe is then transported to the gas chromatograph or the GC/MS. Two samples were taken when the oven reached the desired temperature (i.e. 727 K). These were marked as taken at t=0 minutes at temperature. Samples were taken at intervals of one hour, extending the time between samples as the experiment progressed.

Samples are analyzed using either a gas chromatograph (Hewlett-Packard model number 5890A) with an $Al_2O_3KCl$ PLOT (Porous Layer Open Tubular) capillary column (Chrompack International catalogue number 7517) a thermal conductivity detector (TCD), and a Hewlett-Packard integrator (model number 3392A); or a Hewlett-Packard GC/MS (Gas Chromatograph-/Mass Spectrometer, GC model number 5880A and mass selective detector (MSD), model number 5970B) equipped with a TCD, a crosslinked methyl silicone capillary column and a computer library of 38,791 mass spectra. The operating parameters for the GC were: split flow: 47.60 ml/s; total flow through detector: 11.32 ml/s; reference and column flow: 7.90 ml/s; column flow, alone: 3.87 ml/s; $T_{injector}$ and $T_{detector}$: 150° C.; T column; 130° C., ramped to 200° C.; column head pressure: 10 psi; sample size: 500 μl at atmospheric pressure; and carrier make up gas: He (99.9% pure). The GC/MS operating parameters were: Electron energy: 70 eV; scan range of 10–100 AMU; 10–300 AMU, and 10–550 AMU for respective time periods of 0–20 min; 20–35 min; and 35–45 min; sample size was 500 μl at atmospheric pressure using He carrier makeup gas; temperature of injector: 100° C. temperature detector: 300° C. temperature columns: −80° C., ramped to 200° C.

In addition to the experiments, calculations were made using a flexible computer program. NEWTRAPH, which minimizes the Gibbs free energy of the mixture at prescribed conditions of pressure, temperature, and H to C atomic ratio. The program can handle at least 20 species and up to 5 elements such as H, C, N, O, and S. Any of four equations of state may be used to calculate the fugacity coefficient of each of the species.

These calculations show significant quantities of $C_2$ and higher order hydrocarbons would result at high temperatures (to the full 1000 K), given high enough pressures. A stability boundary (in pressure-temperature space) is mapped out using this program, providing a crude guide as to which conditions will cause a system to undergo thermal decomposition to methane, hydrogen, and/or soot. The calculations of the chemical equilibrium of the experimental systems agree qualitatively with the experimental results.

The following examples represent experiments illustrative of the invention but should not be construed as limiting the invention thereto. Unless otherwise specified, the reactor as described herein was one having a gold plated interior surface; pressures are given in mega pascals; and temperatures in degrees Kelvin.

EXAMPLE 1

Reaction of Propane/Methane Mixtures (20/80)

Using the pressure vessel in the Detailed Description of the Invention, a mixture of 20 percent propane/80 percent methane reacted at 700 K and 60,000 (400 MPa) psi. The results are shown in Table 1. Samples were taken at 95 minutes and 165 minutes. Products were detected by Gas Chromatogram/Mass Spectra GS/MS and reported as detector area fractions. The formation of 2-methyl propane and 2-methyl butane (2-ethyl propane) was noted with the disappearance of trace impurities of ethane and ethylene.

TABLE 1

| GC/MS Output (Numbers given are detector area fractions) Starting Reagents: 20% Propane, 80% Methane, T = 700K, P = 400 MPa | | | | | |
|---|---|---|---|---|---|
| Species | blank | blank | 0 min. | 95 min. | 165 min. |
| methane | .820000 | .801000 | .696000 | .573000 | .920000 |
| $CO_2$ | | .000576 | .000237 | | .001226 |
| ethane | .002000 | .001900 | | | |
| propane | .180000 | .196000 | .303000 | .421000 | .077700 |
| isobutane | | | .000636 | .001520 | |
| butane | | | | .000486 | |
| isopentane | | | | .002790 | .003130 |
| pentane | | | | .000986 | |

EXAMPLE 2

Methane/Propane (50/50)

The procedure of Example 1 was repeated using 50 percent propane/50 percent methane at the temperature of 723 K and a pressure of 60,000 psi (400 MPa). Duplicate samples were taken at 36, 84, 132, 183 and 228 hours. Results by GC/MS (detector area fractions) are shown in Table 2. Despite heavy air contamination, the samples indicated the production of benzene.

TABLE 2

| GC/MS Output from Experiment (Numbers given are detector area fractions) Starting Reagents: 50% Propane, 50% Methane, T = 723K, P = 400 MPa. | | | | | | |
|---|---|---|---|---|---|---|
| Species | blank | blank | 36 hrs | 36 hrs | 84 hrs | 84 hrs |
| methane | .516400 | .582500 | | | .7797 | .940100 |
| $CO_2$ | .000079 | .000241 | .036200 | .133300 | | .000945 |
| ethane | | | .006631 | | | .001243 |

TABLE 2-continued

GC/MS Output from Experiment
(Numbers given are detector area fractions)
Starting Reagents: 50% Propane, 50% Methane,
T = 723K, P = 400 MPa.

| | | | | | |
|---|---|---|---|---|---|
| propane | .479000 | .410600 | .848200 | .375100 | .021200 | .054600 |
| isobutane | .001630 | .001651 | | | | |
| water | .002357 | .005098 | .108900 | .491600 | .199200 | .003189 |
| butane | .000351 | | | | | |

| Species | 132 hrs | 132 hrs | 183 hrs | 183 hrs | 228 hrs |
|---|---|---|---|---|---|
| methane | .928800 | .809986 | .908400 | .894800 | .992000 |
| CO₂ | .000143 | .000229 | .000568 | .000258 | .000931 |
| ethane | .038960 | .020000 | .007376 | .011000 | |
| propane | .027100 | .167700 | .077700 | .085400 | .005833 |
| isobutane | | .000645 | | | |
| water | 004533 | .000745 | .006014 | .007622 | .001264 |
| benzene(?) | .000535 | .008791 | | | |
| hexane(?) | | | | .000850 | |

| reagent assays | methane | CO₂ | propane | isobutane | water | butane |
|---|---|---|---|---|---|---|
| C₃H₈ blank | .00119 | | .99383 | .00115 | | .00383 |
| CH₄ blank | .983800 | .001173 | | | .015100 | |

EXAMPLE 3

Pressure/Temperature Reaction of Methane Alone

In two runs using methane at 673 K and 32,000 psi (213 MPa) for periods of 6 hours and for 2 weeks, no products other than starting methane were detected.

Using the Inconel 718 pressure vessel (having at the time an internal silver coating) shown in FIG. 2, methane (10 ml) was heated at a temperature of 673 K and a pressure of 32000 psi (213 MPa) for a period of 6 hours. No rearrangment or addition products were detected by gas chromatography/mass spectroscopy. Although the samples were tainted by air, this run demonstrated that no rearrangement would take place with a H/C ratio of 4:1 as separately predicted by equilibrium calculations. It was doubted that equilibrium had been reached at this temperature.

The reaction was repeated at 673 K and 32000 psi (213 MPa) for a period of 2 weeks. No rearrangement or addition products were detected. This run was approximately as air free as Example 1; the greater reaction time supports the conclusion that the equilibrium of a hydrocarbon system with an H/C ratio of 4:1 at 673 K and 32,000 psi (213 MPa) lies at methane. The run ended when the RTD used by the oven controller failed.

EXAMPLE 4

Pure Propane

Pure Propane (source Matheson) was heated at 773 K and 60,000 psi (400 MPa). Samples taken at 100, 200 and 250 minutes were analyzed by gas chromatography. Results shown in Table 3 indicate methane increase with time of reaction and production of butane, 2-methyl butane and pentane with decrease in amounts of starting propane.

TABLE 3

GO Output (Numbers given are detector area fractions)
Starting Reagent: Pure Propane, T = 773K, P = 400 MPa

| Species | blank | 0 min. | 100 min. | 200 min. | 250 min. |
|---|---|---|---|---|---|
| methane, TOV | .00336 | .01774 | .16582 | .50597 | .80640 |
| methane, BOV | .00161 | .10389 | .95074 | | |
| ethane, TOV | trace | .00873 | .04207 | .06483 | .07050 |
| ethane, BOV | trace | .08016 | | | |
| propane, TOV | .98940 | .96293 | .77146 | .41556 | .12310 |
| propane, BOV | .99299 | .77880 | .03913 | | |
| butane, TOV | .00294 | .00536 | .01006 | .00641 | |
| butane, BOV | .00352 | .01875 | .00385 | | |
| 2-methyl butane, TOV | | .00384 | .00924 | .00648 | |
| 2-methyl butane, BOV | .00188 | .01718 | | | |
| pentane, TOV | | .00069 | .00068 | | |
| pentane, BOV | | .00123 | .00221 | | |

EXAMPLE 5

Propane

Propane was reacted at 723 K and a pressure of 60,000 psi (400 MPa). Samples taken at 1, 2, 3, 4, 5, 35, 9, 13, 18, 27 and 39 hours were analyzed by GS/MS. Results are shown in Table 4. Major components were reported as detector area fractions while trace products were given in part per million again, as detectors area fractions. For clarification of the production of various higher hydrocarbon species, the GS/MS data from Table 4 are selectively plotted with time in FIG. 4 (1-3 carbon species); FIG. 7 (normal alkenes); FIG. 8 (branched species); FIG. 9 (branched species); FIG. 10 (trace species including benzene, heptane and 1,3-dimethyl transcyclopentane; and FIG. 11 (trace species, cyclohexane, methylcyclohexane, 2,2,3-trimethylbutane etc.).

As soon in Table 4, one or more of the following hydrocarbon products result when propane is heated at 723 K and a pressure of 60,000 psi (400 MPa):

a) methane, ethane, n-butane, isobutane, pentane, isopentane, neopentane, n-hexane, 2-methylpentane, 2,3-dimethylbutane, 2,2-dimethylbutane, n-heptane, 2-methylhexane, 2,2-dimethylpentane, 2,3-dimethylpentane, 2,4-dimethylpentane, 2,2,3-trimethylbutane, 2,3,4-trimethylpentane, heptane, 2-methylheptane, octane, nonane, decane 2,3-dimethylhexane, 2,7-dimethyloctane and their mono and di-unsaturated hydrocarbons comprising 1-propene, 1-butene, 2-methyl-1-propene, 1-pentene, 2-pentene(2), 2-pentene (E), 2-methyl-1-butene; 2-methyl-1-butnee, 2-methyl-2-butene, 1-hexene, 2-methyl-1-pentene, 3-methyl-2-pentene (Z), 2,3-dimethyl-2-butene, 3-hexene (Z), 2,4-dimethyl-1-pentene, 4,5-dimethyl-1-hexene, 3,3-dimethyl-1-hexene, 2,8-dimethyl-1,8-nonadiene, 5-methyl-1-heptene;

b) cyclopentene, 1,3-dimethyltranscyclopentane, 1,2-dimethyltranscyclopentane, 1,1,2-trimethylcyclopropane, cyclophexane, methylcyclohexane, benzene, and methylbenzene.

TABLE 4

GC/MS Data
Starting Reagent: Pure Propane, T = 723K, P = 400 MPa

| Species | 240 min. | 321 min. | 540 min. | 780 min. | 1080 min. | 1620 m |
|---|---|---|---|---|---|---|
| methane | .20670 | .10835 | .76617 | .30507 | .22801 | .26822 |
| carbon dioxide | 618 ppm | 327 ppm | 2799 ppm | 317 ppm | 527 ppm | 420 ppm |
| ethane | .03137 | .10488 | .10790 | .16264 | .18483 | .21772 |
| 1-propene | 262 ppm | 591 ppm | 57 ppm | 787 ppm | | 814 ppm |
| propane | .73409 | .52581 | .16765 | .29843 | .31855 | .25583 |
| 2-methyl | .01946 | .04176 | .01839 | .07113 | .08103 | .08602 |

TABLE 4-continued

GC/MS Data
Starting Reagent: Pure Propane, T = 723K, P = 400 MPa

| Species | 240 min. | 321 min. | 540 min. | 780 min. | 1080 min. | 1620 m |
|---|---|---|---|---|---|---|
| propane | | | | | | |
| 2-methyl 1-propane | 1030 ppm | 3603 ppm | 335 ppm | 2542 ppm | 119 ppm | 2095 ppm |
| butane | .01270 | .03664 | .01028 | .05044 | .05335 | .05295 |
| 2,2-dimethyl propane | | 835 ppm | 336 ppm | 2276 ppm | 4148 ppm | 5062 ppm |
| 1-butene | | 287 ppm | | 272 ppm | 277 ppm | 281 ppm |
| 3-methyl 1-butene | | 170 ppm | | 110 ppm | 85 ppm | 96 ppm |
| 2-methyl butane | .03905 | .04363 | .01087 | .03714 | .03548 | .03359 |
| 1-pentene | | 121 ppm | | 98 ppm | 109 ppm | 102 ppm |
| 2-methyl 1-butane | | 468 ppm | | 332 ppm | 332 ppm | 333 ppm |
| pentane | .01165 | .02165 | 4246 ppm | .02045 | .02457 | .02511 |
| 2-pentene (Z) | | 378 ppm | | 247 ppm | 281 ppm | 265 ppm |
| 2-pentene (E) | | 2201 ppm | | 136 ppm | 154 ppm | 165 ppm |
| 2-methyl 2-butene | 528 ppm | | 162 ppm | 900 ppm | 839 ppm | 804 ppm |
| 2,2-dimethyl butane | 527 ppm | 2193 ppm | 398 ppm | 3323 ppm | 5722 ppm | 6142 ppm |
| cyclopentene | | | | | 18 ppm | 22 ppm |
| 4-methyl 1-pentene | | 133 ppm | | 38 ppm | 50 ppm | 47 ppm |
| 2,3-dimethyl butane | 3631 ppm | 8388 ppm | 687 ppm | 3915 ppm | 5247 ppm | 4489 ppm |
| 2-methyl pentane | .01706 | .03162 | 3592 ppm | .01562 | .01822 | .01535 |
| 4-methyl 1-hexene | 431 ppm | 2040 ppm | 1743 ppm | 2138 ppm | 3986 ppm | 3621 ppm |
| 2-methyl 1-pentene | | 244 ppm | | 110 ppm | 132 ppm | 101 ppm |
| hexane | 8376 ppm | .01944 | 1486 ppm | 7905 ppm | .01108 | 7230 ppm |
| 3-methyl 2-pentene (Z) | | | | 45 ppm | 261 ppm | 172 ppm |
| 2,3-dimethyl 2-butene | | 745 ppm | | 133 ppm | 81 ppm | 40 ppm |
| 3-hexene (Z) | | 145 ppm | | 53 ppm | 56 ppm | 18 ppm |
| 1,1,2-trimethyl cyclopropane | | 170 ppm | | 47 ppm | 77 ppm | 35 ppm |
| 2,2-dimethyl pentane | 341 ppm | 1052 ppm | 24 ppm | 621 ppm | 1415 ppm | 964 ppm |
| 2,4-dimethyl pentane | 6402 ppm | .01279 | 721 ppm | 4215 ppm | 6190 ppm | 3878 ppm |
| 2,2,3-trimethyl butane | 391 ppm | 953 ppm | | 329 ppm | 431 ppm | 234 ppm |
| 2,4-dimethyl 1-pentene | | 144 ppm | | 40 ppm | 25 ppm | |
| benzene | | 299 ppm | | 265 ppm | 777 ppm | 873 ppm |
| 4,5-dimethyl 1-hexene | | 374 ppm | | 224 ppm | 328 ppm | 198 ppm |
| cyclohexane | | | | 159 ppm | 311 ppm | 218 ppm |
| 2-methyl hexane | 8857 ppm | .01851 | 811 ppm | 4507 ppm | 6377 ppm | 3201 ppm |
| 3-methyl hexane | 703 ppm | 2382 ppm | 20 ppm | 1081 ppm | 2026 ppm | 1162 ppm |
| 1,3-dimethyl transcyclopentane | | 607 ppm | | 826 ppm | 1100 ppm | 646 ppm |
| 1,2-dimethyl transcyclopentane | | 707 ppm | | | 410 ppm | 212 ppm |
| heptane | 494 ppm | 2290 ppm | | 565 ppm | 1086 ppm | 479 ppm |
| 3,3-dimethyl 1-hexene | | 16 ppm | | | 8 ppm | |
| 2,8-dimethyl 1,8-nonadiene | | 19 ppm | | | | |
| 2,2-dimethyl hexane | | 35 ppm | | 19 ppm | 86 ppm | 47 ppm |
| methyl cyclohexane | | 682 ppm | | 261 ppm | 597 ppm | 287 ppm |
| 2,7-dimethyl octane | | 495 ppm | | 72 ppm | 206 ppm | 85 ppm |
| 2-undecene (Z) | | 401 ppm | | 76 ppm | 316 ppm | 138 ppm |
| 5-methyl 1-heptene | | 171 ppm | | 23 ppm | 102 ppm | 34 ppm |
| 4,5-dimethyl 1-hexene | | 92 ppm | | | 28 ppm | |
| methyl benzene | | 311 ppm | | 14 ppm | 252 ppm | 136 ppm |
| 2-methyl heptane | | 483 ppm | | 15 ppm | 163 ppm | 49 ppm |
| octane | | 270 ppm | | | 100 ppm | 31 ppm |
| nonane(?) | | 38 ppm | | | 32 ppm | |
| 2-methyl | | 79 ppm | | | | |

TABLE 4-continued

GC/MS Data
Starting Reagent: Pure Propane, T = 723K, P = 400 MPa

| Species | 240 min. | 321 min. | 540 min. | 780 min. | 1080 min. | 1620 m |
|---|---|---|---|---|---|---|
| pentanal | | | | | | |
| decane(?) | | 7 ppm | | | | |

What is claimed is:

1. A process for converting a feedstock consisting essentially of one or more $C_1$-$C_3$ hydrocarbons to product hydrocarbons having up to 12 carbon atoms which comprises heating in the absence of catalyst one or more $C_1$-$C_3$ alkane hydrocarbons at a temperature from about 625 K to about 775 K at a pressure from about 40,000 psi (267 MPa) to about 70,000 psi (467 MPa).

2. The process of claim 1 wherein said feedstock hydrocarbon is selected from the group consisting of methane, ethane, and propane or mixtures thereof; wherein said product comprises at least one of the following: branched or straight chain alkane hydrocarbons; branched or straigh chain unsaturated aliphatic hydrocarbon; cycloalkanes and aromatic hydrocarbons.

3. The process of claim 2 wherein the temperature is about 750 K and the pressure is about 60,000 psi (400 MPa).

4. The process of claim 3 wherein the feedstock is propane.

5. The process of claim 3 wherein the feedstock is methane.

6. The process of claim 1 wherein the feedstock is propane and product hydrocarbons comprise at least one of the following:
   a) methane, ethane, n-butane, isobutane, pentane, isopentane, neopentane, n-hexane, 2-methylpentane, 2,3-dimethylbutane, 2,2-dimethylbutane, n-heptane, 2-methylhexane, 2-methylhexane, 2,2-dimethylpentane, 2,3-dimethylpentane, 2,4-dimethylpentane, 2,2,3-trimethylbutane, 2,3,4-trimethylpentane, heptane, 2-methylheptane, octane, nonane, decane, 2,2-dimethylheane, 2,7-dimethyloctane and their mono and diunsaturated hydrocarbons comprsing 1-propane, 1-butene, 2-methyl-1-propene, 1-pentene, 2-pentene(2), 2-pentene, (E), 2-methyl-1-butene; 2-methyl-1-butnee, 2-methyl-2-butene, 1-hexene, 2-methyl-1-pentene, 3-methyl-2-pentene (Z), 2,3-dimethyl-2-butene, 3-hexene (Z), 2,4-dimethyl-1-pentene, 4,5-dimethyl-1-hexene, 3,3-dimethyl-1-hexene, 2,8-dimethyl-1,8-nonadiene, 5-methyl-1-heptene;
   b) cyclopentene, 1,3-dimethyltranscyclopentane, 1,2-dimethyltranscyclopentane, 1,1,2-trimethylcyclopropane, cyclohexane, methylcyclohexane, benzene, and methylbenzene.

7. The process of claim 1 wherein the feedstock is a mixture of methane and propane.

8. The process of claim 1 wherein the conversion is conducted in a stainless steel reactor having a gold coating deposited thereon.

9. A process for converting propane to higher molecular weight hydrocarbons said process comprising heating propane in the absence of a catalyst at a temperature of about 750 K at a pressure of about 60,000 psi (400 MPa) for a time sufficient to produce one or more hydrocarbons having up to 12 carbon atoms selected from the group consisitng of branched or straight chain alkanes, branched or straight chain unsaturated aliphatic hydrocarbons, cycloalkanes and aromatic hydrocarbons.

10. The process of claim 9 wherein the conversion is conducted in a stainless steel reactor having a gold coating.

11. A process for converting a mixture of methane and propane to higher molecular weight hydrocarbons said process comprising heating in the absence of catalyst the methane/propane mixture in a volume ration of from 5:95 to 95:5 at a temperature of from about 625 K to about 875 K at a pressure of from about 30,000 psi (200 MPa) to about 70,000 psi (467 MPa) to produce one or more higher hydrocarbons having up to 12 carbon atoms selected from the group consisting of branched or straight chain alkanes, branched or straight chain unsaturated aliphatic hydrocarbons, cycloalkanes and aromatic hydrocarbons.

12. A process for synthesizing higher hydrocarbons products by adding $C_1$ or $C_2$ hydrocarbon units to saturated hydrcarbons selected from the group consisting of $C_1$-$C_3$ alkanes which comprise the steps of:
   1) combining in the absence of catalyst $C_114$ $C_3$ alkane hydrocarbon with gaseous methane in a volume ratio of from 5:95 to 95:5 in a gold lined pressure reaction vessel to form a reaction mixture;
   2) heating the mixture at a temperature from about 625 K to about 875 K at a pressure from about 40,000 psi (267 MPa) to about 70,000 psi (467 MPa).

13. A process for converting a feedstock consisting essentially of one or more hydrocarbons to higher product hydrocarbons having up to 12 carbon atoms which comprises heating one or more $C_114$ $C_3$ alkane hydrocarbons at a temperature from about 625K to about 775K at a pressure from about 40,000 psi (267 MPa) to about 70,000 psi (467 MPa).

14. The process of claim 13 wherein said heating takes place in a reaction vessel acatalytic to hydrocarbon addition and reforming reactions.

15. A process for preparing higher hydrocarbons from a feedstock consisting essentially of $C_114$ Cphd 3 alkanes which comprises reacting at least one Cphd 114 Cphd 3 alkane in the absence of catalyst at temperature from about 725K to about 825K at a pressure from about 50,000 (333 MPa) to 65,000 psi (433 MPa).

* * * * *

UNITED STATES PATENT AND TRADEMARK OFFICE
CERTIFICATE OF CORRECTION

PATENT NO. : 5,073,666

DATED : Dec. 17, 1991

INVENTOR(S) : Zemanian et al

It is certified that error appears in the above-identified patent and that said Letters Patent is hereby corrected as shown below:

Claim 2, column 11, line 24, "straigh" should be --straight--.

Claim 6, column 11, line 43, "2,2-dimethylheane" should be --2,2-dimethylhexane--;

Claim 6, column 11, line 45, "1-propane" should be --1-propene--;

Claim 6, column 11, line 47, "2-methyl-1-butnee" should be --2-methyl-1-butene--.

Claim 11, column 12, line 25, "ration" should be --ratio--.

Claim 12, column 12, line 38, "$C_1 14C_3$" should be --$C_1-C_3$--.

Claim 13, column 12, line 48, "$C_1 14C_3$" should be --$C_1-C_3$--.

Claim 15, column 12, line 56, "$C_1 14Cphd114$" should be --$C_1-C_3$--.

Claim 15, column 12, lines 57-58, "Cphd114Cphd3" should be --$C_1-C_3$--.

UNITED STATES PATENT AND TRADEMARK OFFICE
CERTIFICATE OF CORRECTION

PATENT NO. : 5,073,666

DATED : Dec. 17, 1991

INVENTOR(S) : Zemanian, et al

It is certified that error appears in the above-identified patent and that said Letters Patent is hereby corrected as shown below:

Col. 11, line 45, "comprsing" should read --comprising--.

Signed and Sealed this

Twenty-seventh Day of April, 1993

Attest:

MICHAEL K. KIRK

Attesting Officer

Acting Commissioner of Patents and Trademarks